(12) United States Patent
Jonsson et al.

(10) Patent No.: US 7,921,708 B2
(45) Date of Patent: Apr. 12, 2011

(54) ENGINE BLOCK DURABILITY TEST

(75) Inventors: Anders Jonsson, Linköping (SE);
Göran Granqvist, Kungsör (SE); Björn Rabenius, Järna (SE); Jan Linder, Bandhagen (SE); Sven-Eric Stenfors, Enskede (SE)

(73) Assignee: Scania CV AB (Publ) (SE)

( * ) Notice: Subject to any disclaimer, the term of this patent is extended or adjusted under 35 U.S.C. 154(b) by 227 days.

(21) Appl. No.: 12/160,647

(22) PCT Filed: Jan. 31, 2007

(86) PCT No.: PCT/SE2007/050047
§ 371 (c)(1),
(2), (4) Date: Sep. 30, 2008

(87) PCT Pub. No.: WO2007/091962
PCT Pub. Date: Aug. 16, 2007

(65) Prior Publication Data
US 2009/0100938 A1    Apr. 23, 2009

(30) Foreign Application Priority Data
Feb. 9, 2006  (SE) ..................... 0600295

(51) Int. Cl.
*G01M 15/00* (2006.01)
(52) U.S. Cl. ............ 73/114.77; 73/837; 73/808; 73/799
(58) Field of Classification Search ............ 73/794, 73/799, 808, 837, 114.77
See application file for complete search history.

(56) References Cited

U.S. PATENT DOCUMENTS

| 4,637,259 | A  | * | 1/1987  | Jones ........................... 73/794 |
| 5,054,314 | A  | * | 10/1991 | Cofflard et al. ............ 73/116.02 |
| 6,453,750 | B1 |   | 9/2002  | Maddison |
| 6,718,833 | B2 | * | 4/2004  | Xie et al. .................... 73/812 |
| 6,732,591 | B2 | * | 5/2004  | Miles et al. ................. 73/808 |
| 6,813,960 | B1 | * | 11/2004 | Owen et al. ................. 73/808 |
| 6,959,591 | B2 | * | 11/2005 | Meyer et al. ............. 73/116.02 |
| 7,100,457 | B2 | * | 9/2006  | Lee et al. ................. 73/862.474 |
| 7,204,152 | B2 | * | 4/2007  | Woodward et al. ........... 73/794 |
| 7,204,153 | B2 | * | 4/2007  | Phipps ........................ 73/808 |
| 2002/0017144 | A1 | * | 2/2002 | Miles et al. ................. 73/808 |
| 2005/0188772 | A1 |    | 9/2005 | Lee et al. |
| 2007/0169563 | A1 | * | 7/2007 | Hohjo et al. ................. 73/799 |

FOREIGN PATENT DOCUMENTS
JP    11-316174    11/1999

OTHER PUBLICATIONS
International Search Report dated May 7, 2007, issued in corresponding PCT application No. PCT/SE2007/050047.

* cited by examiner

*Primary Examiner* — Lisa M Caputo
*Assistant Examiner* — Freddie Kirkland, III
(74) *Attorney, Agent, or Firm* — Ostrolenk Faber LLP

(57) ABSTRACT

The object of the invention is to provide an alternative method for durability testing of an engine block. The engine block comprises cylinder cavities, which cylinder cavities are separated from each other by intermediate walls, each intermediate wall comprising a bolt hole. The method comprises the step of: removing a test specimen from an area of the intermediate wall of the engine block, such that the test specimen comprises the bolt hole.

25 Claims, 7 Drawing Sheets

A-A

ENGINE BLOCK DURABILITY TEST

CROSS REFERENCE TO RELATED APPLICATION

The present application is a 35 U.S.C. §§371 national phase conversion of PCT/SE2007/050047, filed 31 Jan. 2007, which claims priority of Swedish Application No. 0600295-0, filed 9 Feb. 2006. The PCT International Application was published in the English language.

TECHNICAL FIELD

The present invention relates to a method for preparing a test specimen to be used in a durability test using an engine block, a method for preparing a test assembly to be used in a durability test using an engine block, a method for performing a durability test using an engine block and an engine block being associated with a load/life curve generated by the method for performing a durability test.

BACKGROUND ART

To test and compare durability of engine block walls in engines, several solutions have appeared. One example is to use the principle of the so called Hydro Pulse Testing of engine blocks. This is accomplished by pressurizing the cylinders with hydraulic oil. High pressure hydraulic oil is squeezed into the cylinder at a frequency of up to about 15 Hz. The principle of Hydro Pulse Testing is that dummy internal components are used in order to apply a pulsating force onto the engine block walls. This pulsating force simulates the most significant forces on the engine block structure during operating conditions. A number of tests are subjected to pulsating fatigue at different loads until breakage or until a predetermined number of pulsating cycles has run out. The test results are plotted in a pressure/life diagram. By using a well known mathematical method, e.g. a Wöhler diagram, a curve is fitted to the test results. Thus a pressure/life curve describes the fatigue behavior of the tested material or component under constant amplitude. However, there are some problems with the Hydro Pulse Testing method. The very high oil pressure that is required increases the risks of considerable damage to equipment in case of leakage. It is also hard to obtain the high oil pressures needed today and if the trend of raising cylinder pressure in production engines during combustion continues, it will be even harder in the future. The maximum frequency of testing is comparatively low. The method is very time consuming, a test series of seven blocks which is required for making a reliable pressure/life curve, takes about 4 weeks to run.

JP11316174 shows a test method and a testing device of an engine block bearing part, wherein the durability test of a engine block bearing part is executed by fixing a support member for supporting a shaft arranged in the bearing part to be tested by a vibration exciting plate. Even if this method solves the problem with high oil pressure mentioned above, it has some disadvantages.

In the Hydro Pulse Testing case and in the method in JP11316174 the regions around two bolt holes are stressed simultaneously. This means that when one of them breaks, the other is useless for durability evaluation. At most there are only three test results per block. In a series of approximately 20 test results which is common when making a reliably load/life curve, seven engine blocks are required. The consequence thereof is that the Hydro Pulse Testing case and the case described in JP11316174 have the problem that the engine block consumption is very high. An engine block is very expensive and requires a high energy consumption to produce, and a high consumption of them therefore makes these test methods very expensive.

SUMMARY OF THE INVENTION

It is therefore an object of the invention to provide an alternative method for durability testing of an engine block.

In accordance with the invention, this object is achieved by a method for preparing a test specimen to be used in a durability test using an engine block, where the engine block comprises cylinder cavities, which cylinder cavities are separated from each other by intermediate walls, each intermediate wall comprising a bolt hole. The method comprises the step of: removing a test specimen from an area of the intermediate wall of the engine block, such that the test specimen comprises the bolt hole.

In accordance with the invention, this object is further achieved by a method for preparing a test assembly to be used in a durability test using an engine block, by using a test specimen prepared by means of the test specimen preparing method according to the invention. The method comprises the step of engaging a dummy assembly with the bolt hole of the test specimen, making up the test assembly.

In accordance with the invention, this object is further achieved by a method for performing a durability test using an engine block by using a test assembly prepared by means of the test assembly preparing method according to the invention. The method comprises the step of subjecting the test assembly to a pulsating fatigue test.

In accordance with the invention, this object is further archived by an engine block being associated with a load/life curve generated by the test method according the invention.

Due to the fact that test specimens are removed from the engine block for making a durability test according to the invention instead of applying dummy components, testing elements, etc directly to an undestroyed engine block, an alternative method for durability testing of an engine block is provided.

An advantage of the present is that each bolt hole area in the engine block contributes to the final load/life curve, and can thus be subjected to an individual load case of the operator's choice.

Another advantage of the invention is that it provides a lower cost of testing due to fewer engine blocks being removed from production.

Another advantage of the invention is that the pulsating frequency can be increased which provides increased test capacity due to shorter lead times.

Another advantage of the invention is that the test method gives a less complex load case locally and a more precise stress control in the significant area.

Another advantage of the invention is that it gives a possibility to perform efficient studies of casting parameters as well as other parameters.

MODE(S) FOR CARRYING OUT THE INVENTION

Figure 1:
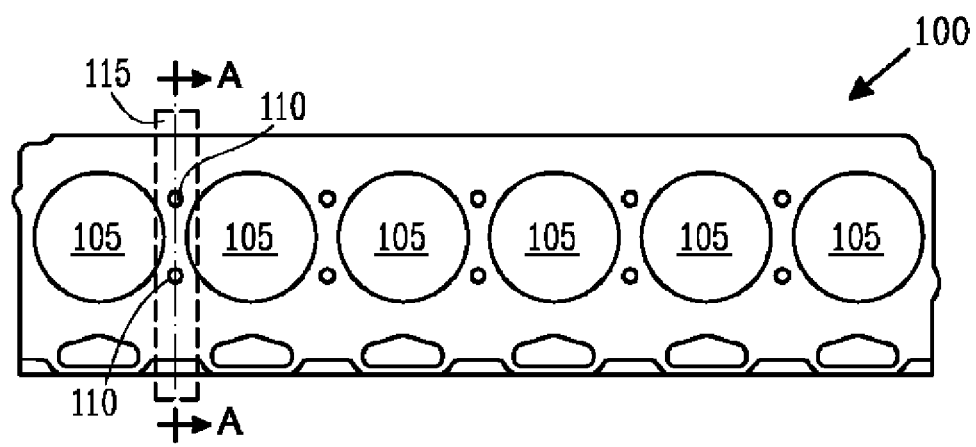
FIG. 1 is a schematic overview over an engine block to be tested according to the invention.

Instead of applying dummy components, testing elements, etc directly to an undestroyed engine block for making durability tests, test specimens are removed from the engine block for making a durability test according to the invention. Fully manufactured engine blocks may be used for making the test specimens. FIG. 1 shows a schematic overview over an engine block 100 seen from above. The engine block 100 may be of different types such as e.g. Inline- or V-blocks. In this example, engine block 100 is an inline engine block which has six cylinder cavities 105, which six cylindrical cavities 105 are separated from each other by intermediate walls. The engine block 100 comprises bolt holes 110. The bolt hole 110 may be a main bearing cap bolt hole or other types of bolt holes such as cylinder head bolt holes, that often are threaded inside. The bolt holes 110 are intended for receiving bolts such as main bearing cap bolts, which main bearing cap bolts in turn keep a crank shaft in place. The design of the engine block 100 is such that cracks under test conditions regularly appear at a thread or at the bottom radii of the bolt holes 110 in the intermediate wall. Therefore the test specimen is removed such that it comprises a bolt hole 110. Commonly and in this example there are two bolt holes 110 for main bearing caps in each intermediate wall. Therefore, an area 115 comprising the intermediate wall is removed from the engine block 100. This may be performed by sawing by means of a cutting machine. The removed area 115 comprising the intermediate wall then comprises two bolt holes 110. In this example with six cylinders, five areas 115 comprising intermediate walls may be removed as depicted by dotted rectangles 115 in FIG. 1.

Figure 2:
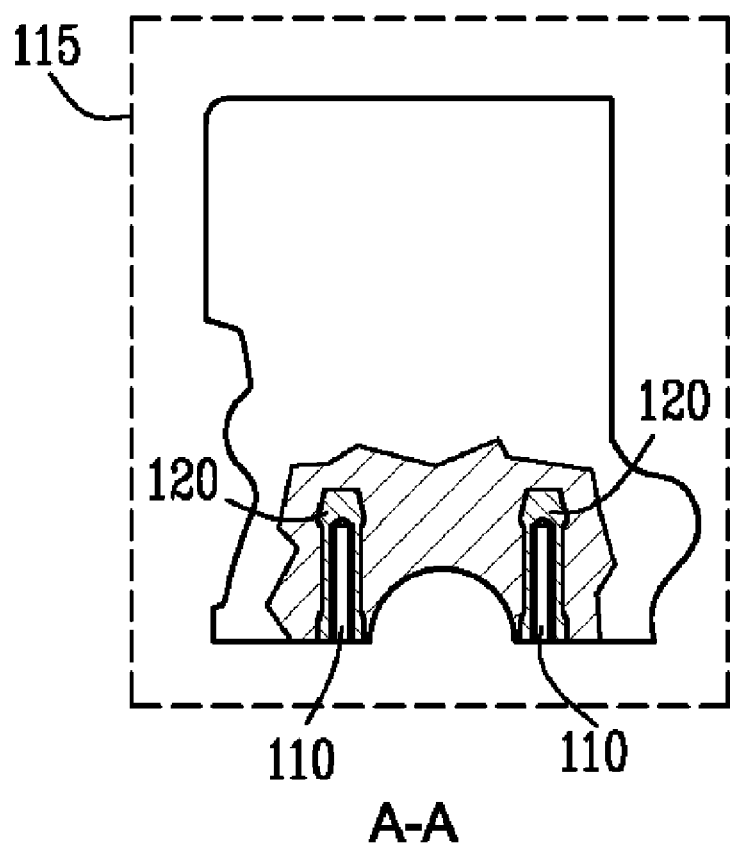
FIG. 2 is a cross section at the line A-A in FIG. 1.

FIG. 2 depicts a cross section of the engine block 100 along line A-A pointed out in FIG. 1, including the intermediate wall 115 to be removed. A test specimen 120 is removed from an area in the intermediate wall 115 which test specimen comprises one bolt hole 110. This may be performed by sawing by means of a cutting machine. As mentioned above and as also can be seen from FIG. 2 the intermediate wall 115 comprises two bolt holes 110. Therefore two test specimens, may be removed from one removed intermediate wall 115, each test specimen 120 being removed from an area that comprises one bolt hole 110. In this example with six cylinders, and with five intermediate walls 115 removed, ten test specimens may be removed from one and the same engine block 100.

Figure 3:
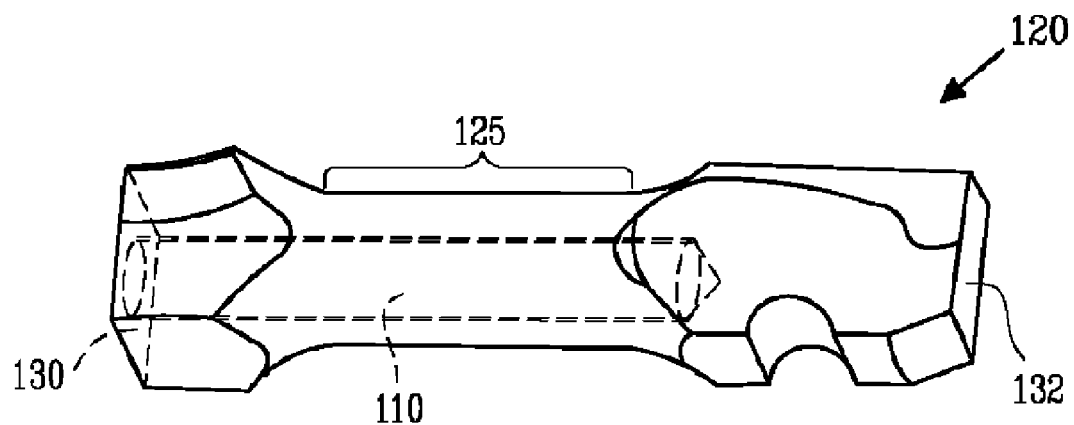
FIG. 3 is a perspective view of a test specimen used in the method according to the invention.

FIG. 3 depicts a perspective view of the test specimen 120. The test specimen is removed such that the bolt hole 110 has its opening in a first end 130 of the test specimen 120, and such that the bolt hole 110 extends in axial direction inside the test specimen 120 for more than half the length of the test specimen 120. The bolt hole 110 is marked with dotted lines in FIG. 3. The test specimen 120 comprises a second end 132, which second end 132 of the test specimen is shaped in a suitable way for engagement with an axial hydraulic fatigue test rig 185 (depicted in FIG. 7). To force the cracks during test to originate from the bolt holes 110, a middle part 125 of the test specimen 120 is turned or cut to circular cross section, making up a cylindrical part of the test specimen 120 such that the bolt hole 110 comprised in the test specimen 120 is coaxial with the cylindrical middle part 125 of the test specimen 120, as shown in FIG. 3. The length of the test specimen 120 may be e.g. 150-300 mm, preferably about 180 mm long. The second end 132 of the test specimen makes up a fixture area to be in engagement with the axial hydraulic fatigue test rig. This second end 132 has a rectangular cross section and has a length that may be varied depending on the type of fixturing equipment and the possible need for manufacturing of tensile test specimens for evaluation of static material properties such as tensile strength, elastic modulus etc. The middle part 125 of the test specimen 120, i.e. the circular cross section of the test specimen 120, may have a diameter of e.g. 28-36 mm, preferably 32 mm and may be 40-100 mm, preferably 60 mm long.

Figure 4:
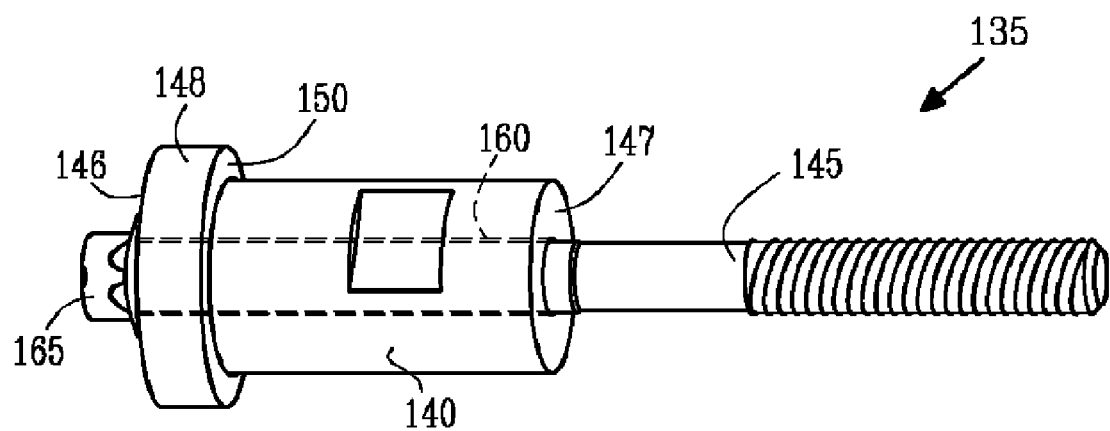
FIG. 4 is a perspective view of a dummy assembly used in the method according to the invention.

In the test method of the invention a dummy assembly 135 is used, depicted in FIG. 4. The word dummy is in this document defined as a replacing element which is prepared for and only used for tests, and which dummy element deludes the engine block 100 into believing that the element is a real element, e.g. deluding the engine block 100 into believing that a dummy element is a real main bearing cap. The dummy assembly 135 comprises a dummy element 140 and a bolt 145. The dummy element 140 is in this example a dummy main bearing cap which is cylindrical. The dummy element 140 may also be another type of dummy element such as a dummy cylinder head. The dummy element 140 comprises a first end 146 and a second end 147. The dummy element 140 comprises in its first end 146 a head 148, i.e. a part having a diameter that is larger than the rest of the dummy element 140. The difference in level of the two different diameters, i.e. of the head 148 and the rest of the dummy element 140, makes up a shoulder 150. The shoulder 150 is intended to hitch on a pulling device 155 (shown in FIG. 6). The dummy element 140 further comprises a through hole 160 in its axial direction. The hole 160 is marked with dotted lines in FIG. 4. The bolt 145 may be a main bearing bolt or another type of bolt such as cylinder head bolt, and comprises a head 165 in its one end and is threaded in its other end. The diameter of the head 165 is larger than the through hole 160 of the dummy element 140 while the diameter of the rest of the bolt 145 has a diameter that is less than the diameter of the through hole of the dummy element 135. The bolt 145 is put through the hole 160 to a position where it is stopped by the head 165 of the bolt 145. The assembled dummy element 140 and bolt 145 makes up the dummy assembly 135 which is shown in FIG. 4.

Figure 5:
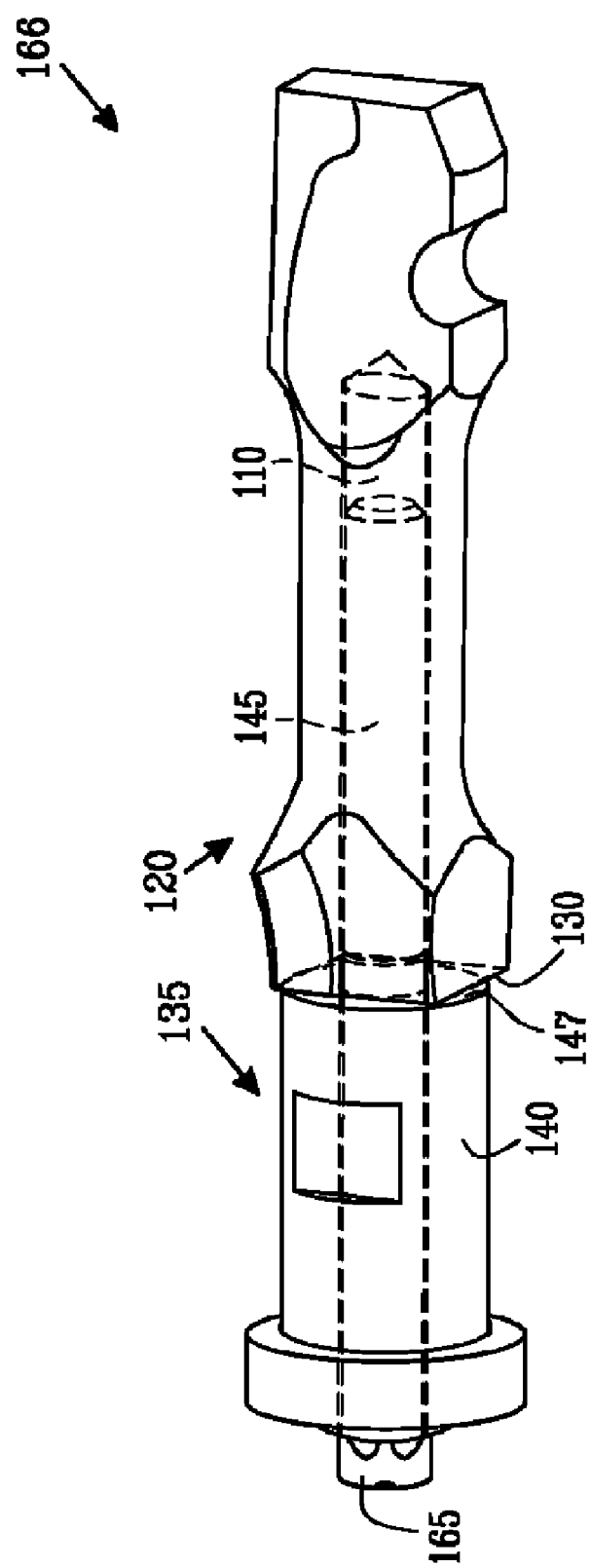
FIG. 5 is a perspective view of a test assembly used in the method according to the invention.

Referring to FIG. 5, the main bearing assembly 135 is then engaged with the bolt hole 110 in the test specimen 120 e.g. by screwing the bolt 145, protruding from the hole 160, into the threaded bolt hole 110 of the test specimen 120. The main bearing assembly 135, engaged with the test specimen 120, makes up a test assembly 166. The bolt 145 is engaged into the bolt hole 110 such that the second end 147 of the dummy element 140 bears against the surface of the first end 130 of the test specimen 120. If the engagement is performed by screwing, it is screwed in with the required torque to simulate a realistic pretension, typically from 50 Newton meter (Nm) plus 90 degrees angular displacement to 200 Nm plus 90 degrees angular displacement.

Figure 6:
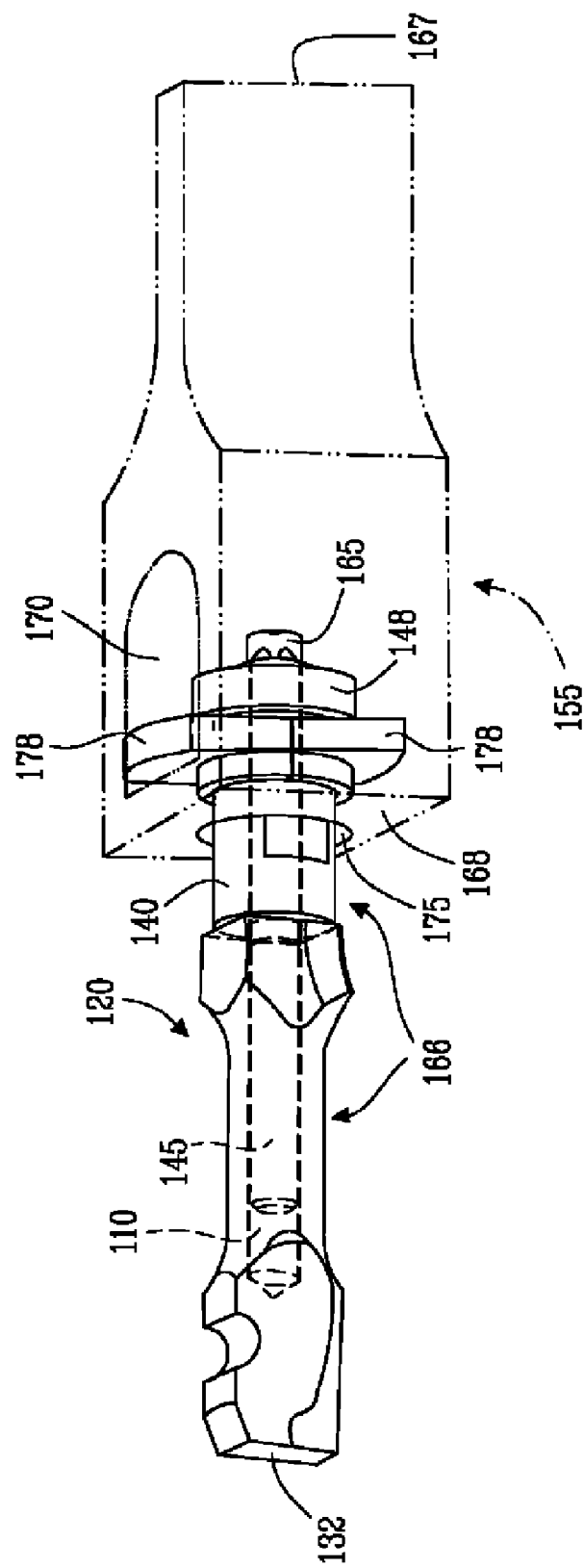
FIG. 6 is a perspective view of a dummy assembly inserted into a special pulling device, used in the method according to the invention.

The engaged main bearing assembly 135 and test specimen 120 is then inserted into a special pulling device 155, shown in FIG. 6. The pulling device 155 comprises a first end 167 and a second end 168. The first end 167 is shaped in a suitable way for engagement with an axial hydraulic fatigue test rig. The pulling device 155 comprises a cavity 170. The cavity 170 comprises an opening 175 in the second end 168 of the pulling device 155, which opening 175 has a diameter being larger then the smallest diameter of the dummy element 140, and may be narrower than the head 148 of the dummy element 140. The dummy element 140 is engaged with the pulling device 155 by being inserted into the cavity 170 of the pulling device 155, having its head 148 inside the cavity 170, extending through the opening 175 and being hitched by the shoulder 150 of the head 148, since the head 148 has too large diameter to pass through the opening 175 of the pulling device 155. The opening 175 may also have a larger diameter than the head 148. In that case two specially designed, securing washers 178 may be used, between the inside of the opening 175 and the shoulder 150 of the head 148 to prevent the head 148 to pass through the opening 175. The engaged main bearing assembly 135 and test specimen 120, i.e. the test assembly 166, is inserted in the pulling device 155. The pulling device 155 may be mounted in the axial hydraulic fatigue test rig before or after the engaged main bearing assembly 135 and test specimen 120 are inserted in the pulling device 155. However, it may be easier to handle the engagement if it is mounted before the engaged main bearing assembly 135 and test specimen 120 are inserted in the pulling device 155.

Figure 7:
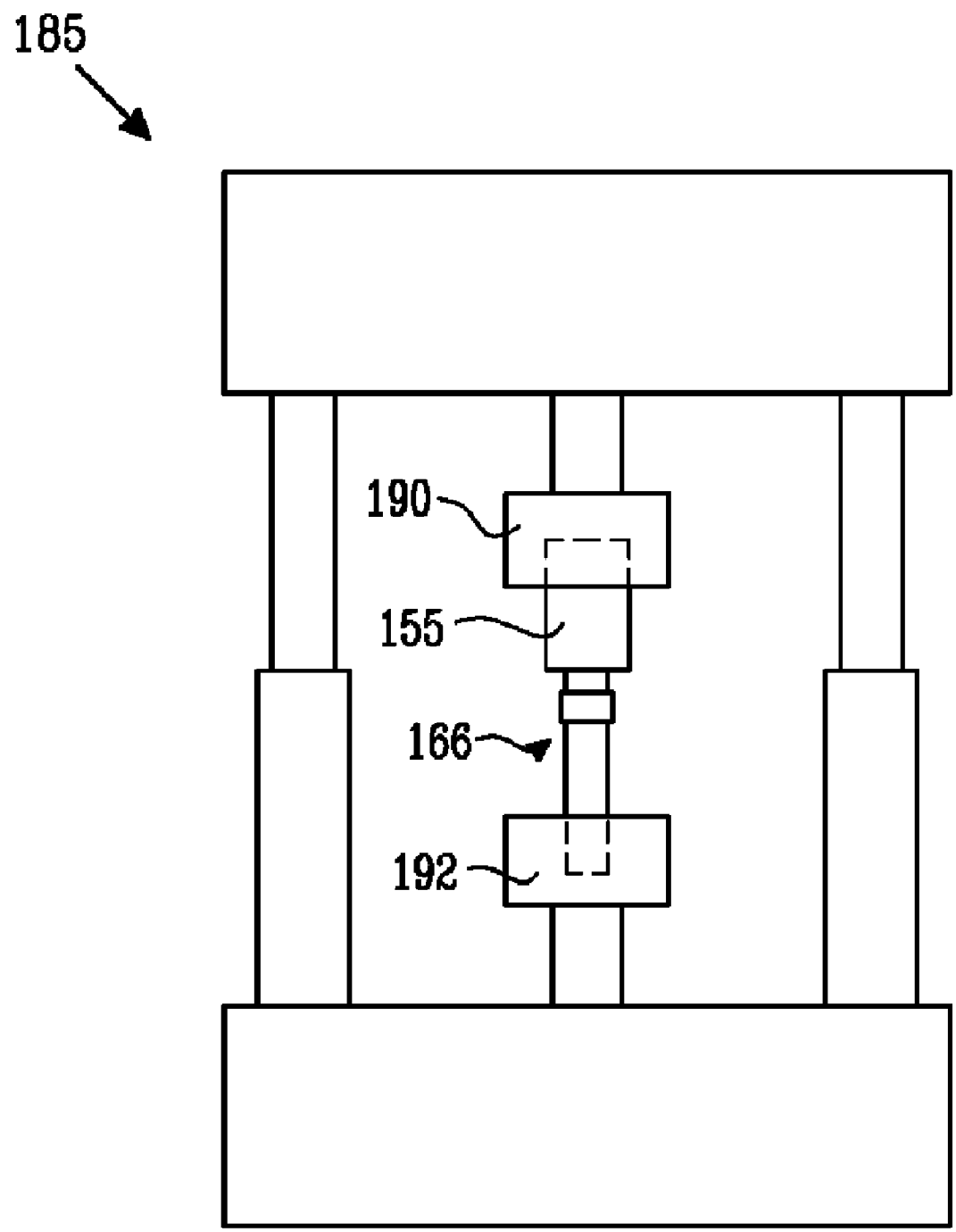
FIG. 7 is a schematic overview over an axial hydraulic fatigue test rig, used in the method according to the invention.

The test assembly 166 is mounted in an axial hydraulic fatigue test rig 185, depicted in FIG. 7. The one end of the test assembly, which is made up of the first end 167 of the pulling device 155 is mounted in a first mounting device 192 of the axial hydraulic fatigue test rig 185. It may be easy to handle if the first end 167 of the pulling device 155 is mounted in the axial hydraulic fatigue test rig before the engaged main bearing assembly 135 and test specimen 120 are inserted in the pulling device 155 as mentioned above. The other end of the test assembly, which is made up of the second end 132 of the test specimen 120 is mounted in a second mounting device 192 of the axial hydraulic fatigue test rig 185. The test specimen 120 is then subjected to pulsating fatigue loads of R>0, e.g. 0.01-0.5, preferably 0.1 where R is the quotient between a minimum load and a maximum load, between which the load is varying, i.e. is pulsating. For making a durability test and forming a load/life curve for an engine block, a series of tests at different loads are required, e.g. 3-35 tests and preferably 20 tests. The word life is in this document defined as the number of cycles to failure for a test specimen. In one example using an engine block made of grey cast iron, the different loads may be such that the used maximum load series is selected between 50 and 80 kilo Newton (kN). The used minimum loads are determined by the chosen R-value. The pulsating frequency may be from 1 Hz and upwards. Since test time is to be kept as short as possible, it is preferable to use as high frequencies as 50 Hertz (Hz) which have been tested successfully. However, frequencies up to about 100 Hz may be possible to use. The test specimen 120 may be cycled up to a predetermined number of cycles, e.g. $5*10^5 - 2*10^7$ cycles, preferably $2*10^6$ cycles, and then be considered run out, i.e. the test is stopped when the test specimen 120 have run the predetermined number of cycles without breaking. In a reliable test series, the predetermined number of cycles are decided such that most of the specimens fails before the predetermined number of cycles has been reached. The load level and the number of cycles to failure are recorded as test results for each specimen. The test results are then plotted into a load/life curve. The load/life curve is finally used for comparison of durability properties in different engine blocks, e.g. blocks of different materials and designs.

As mentioned above, test specimens can be taken out from an inline engine block which has six cylindrical cavities. That means a series of 20 tests only requires two engine blocks which implies a small consumption of engine blocks. A series of 20 tests using the frequency of 50 Hz and a predetermined number of cycles of $2*10^6$ cycles takes only about one week, which is a short time. This means a faster determination of engine block quality.

In this way, an engine block may have a load/life curve generated by the test method according to the invention. Different engine blocks or types of engine blocks may be tested in different test series generating respective different load/life curves.

Figure 8:
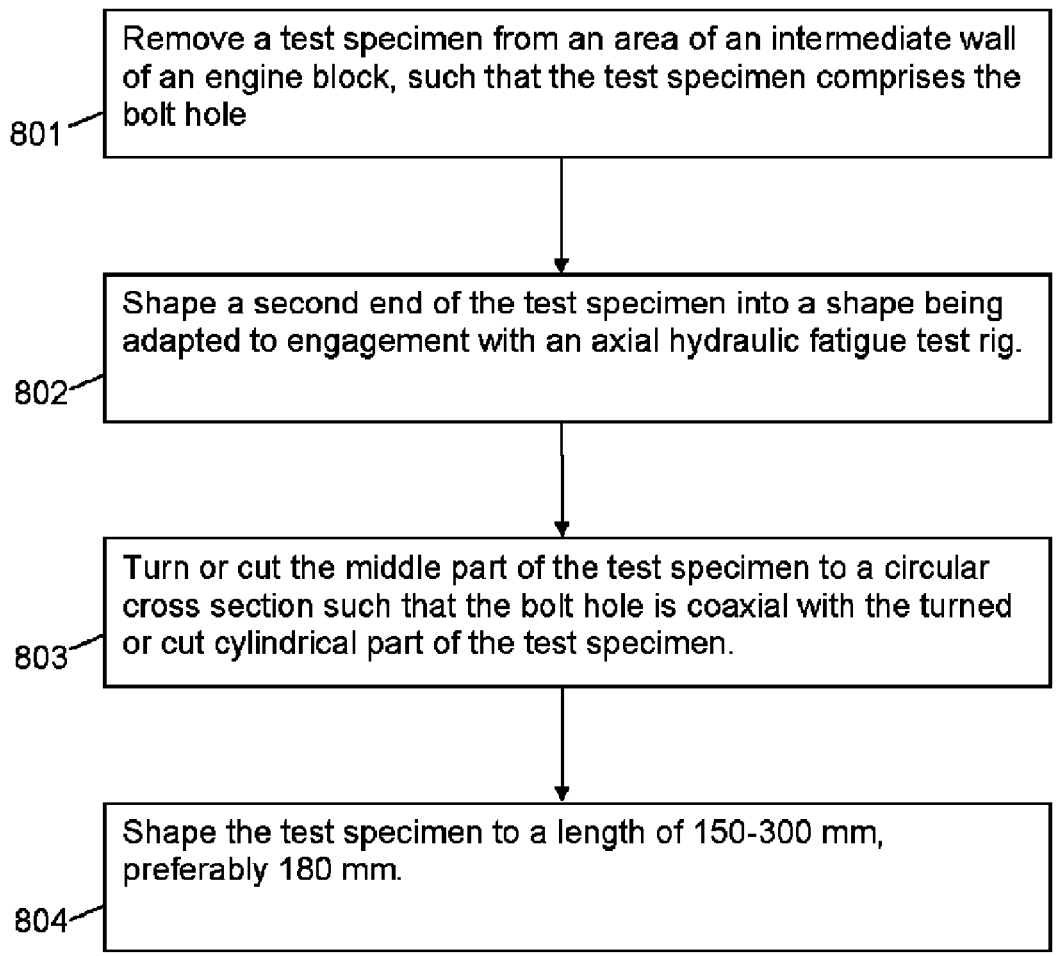
FIG. 8 is a flowchart depicting a method for preparing a test specimen according to the invention.

The method for preparing a test specimen 120 to be used in a durability test using an engine block 100 according to the invention, will now be briefly described referring to FIG. 8. The method comprises the following steps:

801) The test specimen 120 is removed from an area of the intermediate wall 115 of the engine block, such that the test specimen 120 comprises the bolt hole 110.
802) A second end 132 of the test specimen is shaped 120 into being adapted to engagement with an axial hydraulic fatigue test rig (185).
803) The middle part 125 of the test specimen 120 is turned or cut to a circular cross section such that the bolt hole 110 comprised in the test specimen 120 is coaxial with the turned or cut cylindrical part 125 of the test specimen 120.
804) The test specimen 120 is shaped to a length of 150-300 mm, preferably 180 mm.

Figure 9:
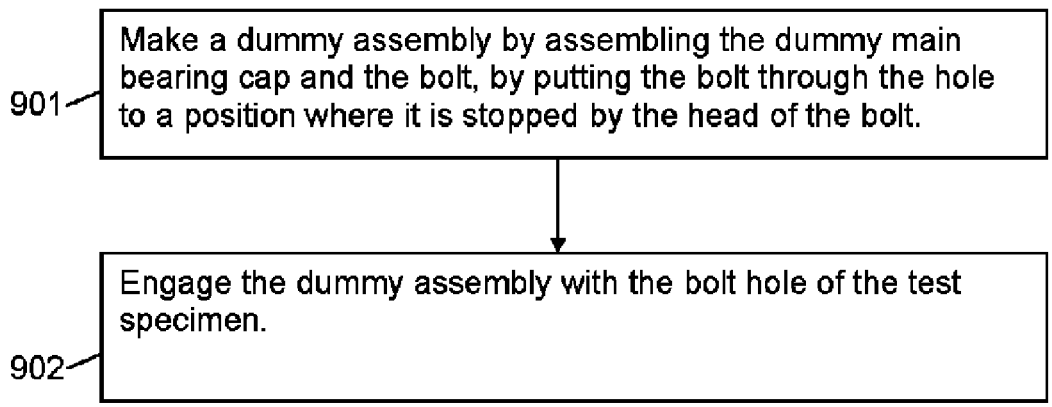
FIG. 9 is a flowchart depicting a method for preparing a test assembly according to the invention.

The method for preparing a test assembly 166 to be used in a durability test using an engine block 100, according to the invention, will now be briefly described referring to FIG. 9. The method uses a test specimen 120 prepared by means of the method according to method steps 801-804 above, and comprises the steps of:

901) The dummy element 140 and the bolt 145 are assembled by putting the bolt 145, through the hole 160 to a position where it is stopped by the head 165 of the bolt 145, the assembled dummy element 140 and a bolt 145 making up the dummy assembly 135.
902) The dummy assembly 135 is engaged with the bolt hole 110 of the test specimen 120, making up the test assembly 166.

Figure 10:
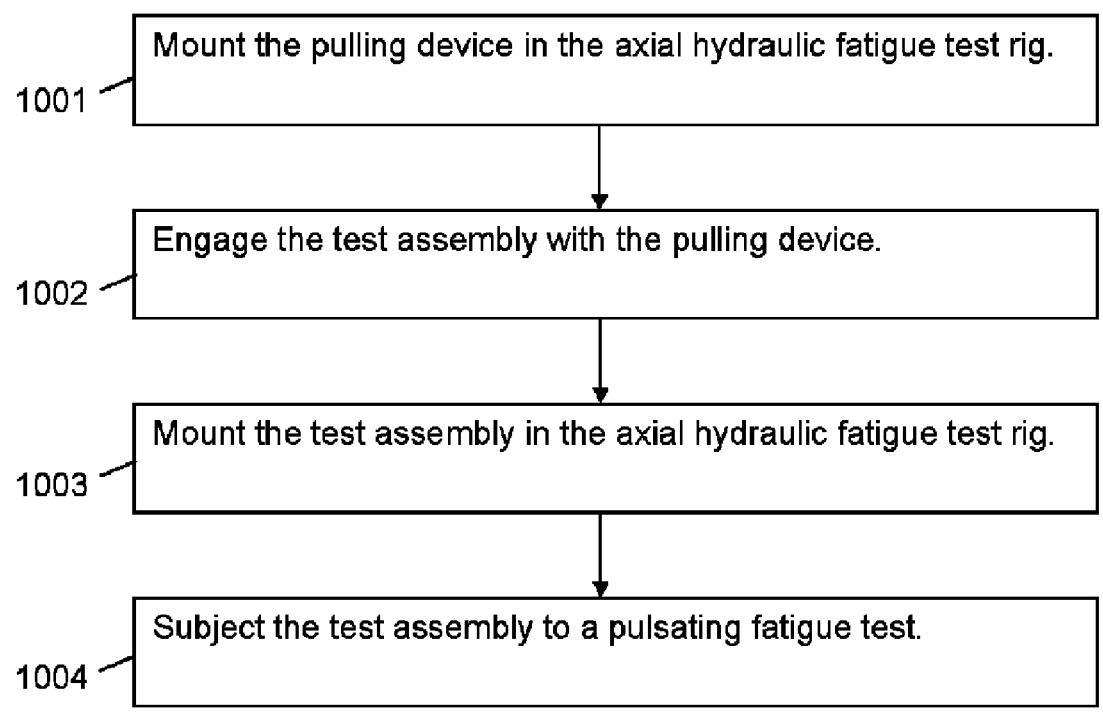
FIG. 10 is a flowchart depicting a method for performing a durability test according to the invention.

The method for performing a durability test using an engine block 100, according to the invention, will now be briefly described referring to FIG. 10. The method uses a test assembly 166 prepared by means of the method according to method steps 901-902 above, and comprises the steps of:

1001) The pulling device 155 is mounted in the axial hydraulic fatigue test rig 185.
1002) The test assembly 166 is engaged with the pulling device.
1003) The test assembly 166 is mounted in the axial hydraulic fatigue test rig 185.
1004) The test assembly 166 is subjected to a pulsating fatigue test.

The invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A method for preparing a test specimen for a durability test of an engine block, wherein the engine block comprises cylinder cavities and the cylinder cavities are separated from each other by intermediate walls, each intermediate wall comprising a bolt hole positioned inside the intermediate wall, the method comprising:
   removing the test specimen from the engine block such that the test specimen comprises at least a portion of the intermediate wall of the engine block and includes the bolt hole.

2. The method according to claim 1, wherein the test specimen comprises a first end and a second end positioned remote in an axial direction from the first end, and the removing is performed such that the bolt hole has an opening in the first end of the test specimen and extends in the axial direction inside the test specimen.

3. The method according to claim 1, further comprising shaping the second end of the test specimen into a shape configured to engage an axial hydraulic fatigue test rig.

4. The method according to claim 3, comprising turning or cutting a middle part of the test specimen between the first and the second ends thereof to a circular cross section such that the bolt hole comprised in the test specimen is coaxial with the turned or cut cylindrical part of the test specimen.

5. The method according to claim 4, wherein the turning or cutting of the test specimen results in a circular cross section having a diameter of 28-36 mm.

6. The method according to claim 4, further comprising shaping the test specimen to a length of 150-300 mm.

7. The method according to claim 1, further comprising engaging a dummy assembly with the bolt hole of the test specimen,
   wherein a test assembly comprises the dummy assembly engaged with the test specimen.

8. The method according to claim 1, further comprising:
   providing a dummy element comprising a through hole oriented in an axial direction of the dummy element, and providing a bolt comprising a head positioned at one end of the bolt; and
   assembling the dummy element and the bolt by putting the bolt through the through hole to a position where the bolt is stopped by the head of the bolt, whereby the assembled dummy element and a bolt comprise a dummy assembly.

9. The method according to claim 7, wherein the dummy assembly comprises a bolt and a dummy element having a through hole, the bolt protruding from the through hole, and
   wherein engaging the dummy assembly with the bolt hole of the test specimen comprises engaging the bolt into the bolt hole of the test specimen such that a second end of the dummy element bears against a surface of the first end of the test specimen.

10. The method according to claim 9, wherein engaging the bolt into the bolt hole of the test specimen comprises screwing the bolt with a torque in a range of 50 Newton meter (Nm) plus 90 degrees angular displacement to 200 Nm plus 90 degrees angular displacement.

11. A method for performing a durability test using an engine block comprising subjecting a test assembly prepared by the method according to claim 7, wherein the durability test is a pulsating fatigue test.

12. The method according to claim 11, further comprising mounting a pulling device in an axial hydraulic fatigue test rig.

13. The method according to claim 12, further comprising engaging the test assembly with the pulling device.

14. The method according to claim 11, further comprising mounting the test assembly in the axial hydraulic fatigue test rig.

15. The method according to claim 11, wherein the subjecting of the test assembly to the pulsating fatigue test is performed by pulsating fatigue loads of R>0, where R is the quotient of a minimum load and a maximum load to which the test assembly is subjected.

16. The method according to claim 11, wherein subjecting of the test assembly to the pulsating fatigue test is performed at a pulsating frequency of 1-100 Hz.

17. The method according to claim 11, further comprising ending the subjecting of the test assembly to the pulsating fatigue test after a predetermined number of cycles.

18. The method according to claim 17, wherein the predetermined number of cycles is in a range of $5 \times 10^5$ to $2 \times 10^7$ cycles.

19. The method according to claim 11, further comprising preparing a plurality of test specimens by removing each test specimen of the plurality of test specimens from the engine block such that each test specimen comprises at least a portion of one of the intermediate walls and a bolt hole inside the one of the intermediate walls;
   engaging a dummy assembly with the bolt hole of each test specimen; and
   performing a series of tests on the plurality of test specimens at different loads and plotting in a load/life curve a load level and a number of cycles to failure.

20. An engine block produced according to the load/life curve generated by the durability tests according to claim 19.

21. The method of claim 1, comprising turning or cutting a middle part of the test specimen between the first and the second ends thereof to a circular cross section such that the bolt hole comprised in the test specimen is coaxial with the circular cross section of the test specimen.

22. The method of claim 4, wherein the turning or cutting of the test specimen results in a circular cross section having a diameter of 32 mm.

23. The method of claim 4, further comprising shaping the test specimen to a length of 180 mm.

24. The method of claim 18, wherein the predetermined number of cycles is $2 \times 10^7$ cycles.

25. A method for preparing a test specimen for a durability test of an engine block, wherein the engine block comprises cylinder cavities separated from each other by intermediate walls, each intermediate wall comprising a bolt hole positioned inside the intermediate wall, the method comprising:
   removing the test specimen from the engine block such that the test specimen comprises at least a portion of the intermediate wall of the engine block and the bolt hole, the test specimen comprising a first end and a second end positioned remote in an axial direction from the first end, and the removing is performed such that the bolt hole has an opening in the first end of the test specimen and extends in the axial direction inside the test specimen;
   shaping the second end of the test specimen into a shape configured to engage an axial hydraulic fatigue test rig, and
   cutting a middle part of the test specimen between the first end and the second end to a circular cross section such that the bolt hole is coaxial with the cut cylindrical part of the test specimen.

* * * * *